United States Patent
Ammann et al.

(10) Patent No.: US 7,290,434 B2
(45) Date of Patent: Nov. 6, 2007

(54) METHOD AND DEVICE FOR DETERMINING THE CONDITION OF A MEASURING PROBE

(75) Inventors: Jürgen Ammann, Zürich (CH); Alfred Peer, Cham (CH); René Oberlin, Würrenlos (CH); Klaus-Dieter Anders, Oberrohrdorf (CH); Christian Zwicky, Gockhausen (CH)

(73) Assignee: Mettler-Toledo AG, Greifensee (CH)

( * ) Notice: Subject to any disclaimer, the term of this patent is extended or adjusted under 35 U.S.C. 154(b) by 199 days.

(21) Appl. No.: 11/017,676

(22) Filed: Dec. 22, 2004

(65) Prior Publication Data

US 2005/0166660 A1    Aug. 4, 2005

(30) Foreign Application Priority Data

Dec. 23, 2003   (EP) ................... 03104932

(51) Int. Cl.
*G01N 21/00* (2006.01)
(52) U.S. Cl. ...................................... 73/1.06
(58) Field of Classification Search ................. 73/1.18, 73/1.01, 1.02, 1.06, 1.57, 1.73, 1.82, 1.83; 204/401; 324/763, 764, 537; 374/142, 45, 374/57
See application file for complete search history.

(56) References Cited

U.S. PATENT DOCUMENTS

| | | | |
|---|---|---|---|
| 4,652,451 A | | 3/1987 | Leedham et al. |
| 5,310,524 A | * | 5/1994 | Campbell et al. ............. 422/33 |
| 5,880,361 A | * | 3/1999 | Taniguchi ................... 73/118.1 |
| 6,173,600 B1 | | 1/2001 | Harada et al. |
| 6,792,390 B1 | * | 9/2004 | Burnside et al. ............ 702/183 |
| 6,807,851 B2 | * | 10/2004 | Wakahara et al. ......... 73/118.1 |
| 6,992,488 B2 | * | 1/2006 | Lin ............................ 324/438 |
| 2002/0120750 A1 | | 8/2002 | Nidd |

FOREIGN PATENT DOCUMENTS

DE    101 00 239 A1    7/2002

(Continued)

OTHER PUBLICATIONS

"Process-Analytical Systems Solutions for the Brewery", company publication of Mettler-Toledo GmbH, CH-8902 Urdorf, Article No. 52 900 309, printed Sep. 2003.

(Continued)

*Primary Examiner*—Robert Raevis
(74) *Attorney, Agent, or Firm*—Buchanan Ingersoll & Rooney PC (57) ABSTRACT

An exemplary method is disclosed which serves to determine a condition of at least one measuring probe which is integrated in a process vessel of a process system with one or more system stages and which is cleaned from time to time using, for example, CIP- and SIP processes, without uninstalling the measuring probe for the cleaning. The temperature of the measuring probe or of the medium surrounding the measuring probe can be measured by a measuring sensor arranged inside or outside the measuring probe, and the condition of the measuring probe can be determined based on a record of the temperature ($T_{S/M}$) measured over the time when the measuring probe is in operation. In some cases, the method can include monitoring correct execution of the CIP- and SIP processes.

16 Claims, 3 Drawing Sheets

FOREIGN PATENT DOCUMENTS

DE  101 41 408 A1  3/2003
DE  102 09 318 A1  9/2003

OTHER PUBLICATIONS

Dr.-Ing. Karl Welchner, "The Top Commandment, A Reproducible Cleaning Process for Process Systems as Core Quality Criterion" (Part 1) Pharma + Food Feb. 2000.

Jochen Endress, "Non-stop in Action",Pharma + Food Jan. 2002.

U. Tietze, Ch. Schenk , "Halbleiterschaltungstechnik" (Semiconductor Circuit Design), 11$^{th}$ edition, 2$^{nd}$ printing, published by Springer Verlag, Berlin 1999.

Product news received on Oct. 18, 2000 from Mettler-Toledo PH Electrode With Integral Temperature Sensor.

Pharmaceutical News—Perspectives in Liquid Process Analytics—"The New $0_2$ Range Of Sensors"—Mettler-Toledo, 8 pages.

"The InFit® CIP Series: Sanitary Design For The Most Exacting Requirements", company publication of Mettler-Toledo GmbH, CH-8902 Urdorf, Article Number 52 400 526, printed May 1999.

Product Sheet "InPro 2000 pH Electrodes with Liquid Electrolyte and Integrated Temperature Sensor", company publication of Mettler-Toledo GmbH, CH-8902 Urdorf, printed Oct. 2000.

Product news received on Oct. 18, 2000 from Mettler-Toledo Self-Cleaning Sensor in PH Control.

* cited by examiner

METHOD AND DEVICE FOR DETERMINING THE CONDITION OF A MEASURING PROBE

CROSS REFERENCE TO RELATED APPLICATIONS

This application claims priority under 35 U.S.C. §119 to European Application No. 03104932.3 filed in Europe on 23 Dec. 2003, the entire contents of which are hereby incorporated by reference in their entirety.

BACKGROUND

The invention relates to a method for determining the condition of a measuring probe, and to a measuring probe and a single-stage or multi-stage process system which are compatible with the practice of the method.

The control of industrial processes, for example in the chemical and pharmaceutical industries, in the textile industry, in the food and beverage industries, in the processing of paper and cellulose, or in the fields of water processing and waste water treatment, is based on the measurement of process variables that are determined by means of suitable measuring probes or sensors.

Reference [1], "Process-Analytical Systems Solutions for the Brewery", a company publication of Mettler-Toledo GmbH, CH-8902 Urdorf, Article No. 52 900 309, with a printing date of September 2003, describes how suitable measuring probes are used in the individual stages of a process chain of a brewery (i.e., in the water processing stage; the brew house; the fermentation and storage cellar; the filtration-, carbonization- and filling stages; as well as the waste water treatment stage) to determine the conductivity, the amount of dissolved oxygen, the pH value, the $CO_2$ value, and the turbidity of the process liquid.

The signals of the measuring probes are transmitted by way of measurement converters (also referred to as transmitters) and in some cases through couplers and a common data bus to a process computer or a central computer which evaluates the measuring signals and controls the process.

It should be noted that with the high level of automation that exists in the fields of food technology and biotechnology, the production systems are in most cases closed systems with permanently installed pipe conduits in which numerous measuring probes are used. Surfaces that are not adequately disinfected and sterilized present health risks. Contamination deposits favor the breeding of undesirable microorganisms as they offer ideal conditions for growth in the form of nutrients and a suitable temperature. Furthermore, microorganisms in deposits are more difficult to deactivate. Completely cleaned surfaces are therefore a fundamental prerequisite for disinfecting and sterilizing a process system. The cleaning of process systems has therefore become a complex procedure and its technical realization has become a demanding task (see [2], Dr.-Ing. Karl Welchner, "The Top Commandment, A Reproducible Cleaning Process for Process Systems as a Core Quality Criterion" (Part 1) Pharma+Food 2/2000).

For a trouble-free process control, it is further of particular importance to monitor the condition of the individual measuring probes as their properties normally change after an extended period of operation.

Reference [3], DE 102 09 318 A1, describes that the wear on a measuring probe manifests itself through a change of one or more parameters that are relevant to the correct functioning of the probe. It is proposed to determine the wear-dependent remaining operating time of a pH- or oxygen probe from its calibration parameters, specifically the zero point, the slope, the impedance and the settling time.

In [4], DE 101 00 239 A1, a method is described for determining the remaining operating time of a potentiometric measuring probe which contains an electrolyte as well as a primary and a secondary reference element that are arranged in such a manner that an electrolyte deficiency which advances from an opening of the measuring probe can be detected by means of a secondary reference element before the electrolyte deficiency reaches the primary reference element which interfaces with a voltage potential that is to be measured. After the difference between the potentials measured at the primary and secondary reference elements has exceeded a given limit value, the remaining operating time can be determined and indicated.

The aforementioned reference [4] further describes how contaminations can occur on measuring probes that are used for the monitoring of chemical or microbiological processes, whereby errors can be introduced in the measuring result. Contaminating deposits will therefore have to be removed not only in the process system or its individual components but also from the measuring probes in order to ensure correct measuring results as well as an uncompromised sanitary state of the process system. Because of the large number of measuring probes used in such systems, they are normally not uninstalled for the cleaning, but are cleaned and sterilized with a CIP- (Cleaning In Place) or SIP- (Sterilizing In Place) process. The CIP processes prevent any bacterial growth, and the pipe conduit is freed of contaminating particles after the end of the process. The process consists of pumping either a cleaning/disinfecting liquid or simply hot water through the pipe conduit system.

CIP- compatible measuring probes, conductivity sensors, pH sensors, $O_2$ sensors, $CO_2$ sensors, and turbidity sensors as well as suitable armatures and process system connectors are disclosed in [1]. Also shown in reference [1] are control modules (EasyClean) which offer a solution to realize automated cleaning and calibrating systems.

The interval time between calibrations of an electrochemical measuring probe can be determined for example through a procedure as described in [5], DE 101 41 408 A1. A basic time interval is prescribed for a defined basic range of values of at least one measurement parameter of a medium to be measured, which parameter is relevant to the adaptation of the calibration interval and is monitored during the operation of the measuring probe. Subsequently, the deviation of the detected measuring parameter values from the defined basic range of values is determined, and the calibration time interval is adapted dependent on the detected deviation.

Thus, according to references [3] and [4], the condition of the measuring probes is determined from changes in the properties of the measuring probes. Reference [5] teaches a method of determining the time intervals within which the measuring probes have to be recalibrated in order to compensate for changes that may have occurred.

As described above, these procedures involve considerable effort and expense and may in some cases require a compatible design of the measuring probes.

It is also known that measuring probes should be exchanged after a certain number of CIP- or SIP cycles.

As disclosed in reference [6], Jochen Endress, "Non-stop in Action", Pharma+Food 1/2002, page 36, the allowable cumulative CIP exposure times are different for individual measuring probes. It is further possible that CIP- or SIP processes are not performed in all parts of a process system.

Also, the CIP- or SIP processes in the individual parts of the system may differ for example in regard to the temperature being used, so that wear conditions of different severity occur in the different parts. It is also possible that different cleaning processes are performed sequentially in a process system stage. As an example, each time a number n of CIP processes have been performed, an SIP process is executed. Thus, considering all possible variations of the processes running in a system, in particular the CIP- and SIP processes, the administration of the measuring probes of an entire process system becomes very complicated and expensive. On the other hand, information that is simply based on an overall count of how many CIP- and SIP processes have been initiated is not precisely representative of the condition of the measuring probes used in the system.

All of the foregoing documents mentioned are hereby incorporate by reference in their entireties.

SUMMARY

A method is disclosed of determining the condition of a measuring probe that is integrated in a process vessel, wherein the measuring probe is cleaned from time to time, particularly by using state-of-the-art CIP- or SIP processes, without uninstalling the probe. A measuring probe as well as a process system that includes the process vessel with the measuring probe and a measurement- and/or control device is disclosed which is compatible with the use of the method.

The term "process vessel" in the present context refers to a device in which one or more measuring probes can be installed, for example a mixing cauldron, a fermentation tank, a reactor, or a flow-through pipe of a conduit system, or another device that is suitable for the installation of a measuring probe, as shown, e.g., in reference [1].

An exemplary method disclosed herein is simple to perform and delivers precise status information for each measuring probe installed in the process vessel or process system.

An exemplary method serves to determine the condition of at least one measuring probe which is integrated in a process vessel and which, in its installed state, is cleaned from time to time, in particular by means of known CIP- and SIP processes. The method can be performed in large or small systems of any kind equipped with a process vessel and a measuring probe, including for example a fermentation tank or a reactor.

A measurement sensor arranged inside the measuring probe or inside the process vessel can be used to measure the temperature of the measuring probe or of the medium surrounding or flowing around the measuring probe. Based on the recorded time profile of the measured temperature during the operating time of the measuring probe, the condition of the latter can be determined.

In an exemplary embodiment, the temperature is compared to at least one threshold value. When the threshold has been exceeded:
a) the presence of a wear-generating load associated with the threshold is registered;
b) the presence of a wear-generating load associated with the threshold is registered and the cumulative sum of all wear-generating loads is determined;
c) the presence of a wear-generating load associated with the threshold is registered, the cumulative sum of all wear-generating loads is determined, and by comparing the sum to a maximum value for the allowable lifetime wear-generating load, an allowable remaining wear-generating load or remaining operating lifetime is determined.

For example, after a wear-generating load has been determined, the registered remaining operating lifetime is reduced accordingly. The allowable remaining wear-generating load or remaining operating lifetime correlates for example to the allowable remaining number of CIP- or SIP processes. However, if the CIP- or SIP processes are set to run under a fixed time schedule, the point in time or the date can be determined when the measuring probe will have to be exchanged or recalibrated.

Thus, an exemplary method as disclosed herein makes it possible to individually determine for all measuring probes in a complex process system the allowable remaining wear-generating load or remaining operating life until replacement, maintenance service and/or recalibration, as the actual wear effects on the measuring probes can be detected, registered and processed in a cost-effective manner.

An exemplary method as disclosed herein has the capability to keep track of CIP- or SIP processes as well as wear-generating work processes performed with a process material. Costs associated with the analysis of certain parameters of the measuring probe, for example for the use of additional measuring probe elements such as secondary electrodes, can be avoided when using this method. Furthermore, the wear-generating load of the respective measuring probes does no longer need to be calculated from the processes that are in some cases initiated locally by the process control program, and from their process parameters, which would involve a task of considerable cost and complexity and would be prone to numerous possible errors. Instead of calculating the operating lifetime of the measuring probes based on the processes initiated at the process control level, the operating life of the measuring probes can be determined from the actually occurring wear effects.

By using threshold values it is possible to identify processes that have been initiated and to take the associated wear-generating loads into account in the individual calculation of the allowable remaining wear-generating load or remaining operating life. The values for the pressure and temperature levels used in the CIP- and SIP processes are widely variable and depend on the specific area of application. For example, the CIP temperatures used in milk-processing systems are around 80° C. The appropriate temperature level for SIP processes depends on whether or not a disinfectant is being used. For example, the temperature level chosen for SIP processes is about 20° C. higher than for CIP processes. SIP processes in the field of biotechnology, for example, are performed at 120° C., while SIP processes in the food industry are performed at about 95° C.

By using two appropriately selected threshold values, it is possible to differentiate between CIP- and SIP processes that may follow each other in a sequence and to calculate the respectively different changes in the remaining operating life or the allowable remaining wear-generating load. Thus, it is possible to register for each detected process a corresponding reduction in the remaining operating life or the allowable remaining wear-generating load of a measuring probe.

In exemplary embodiments, the time integral of the measured temperature is calculated either overall or only from the time when a threshold has been exceeded. If the overall temperature profile is considered, it is possible for example to take additional processes besides cleaning processes into account in the calculation of the remaining operating life or the allowable remaining wear-generating load. The remaining operating life or the allowable remaining wear-generating load can subsequently be determined by taking the difference between the integral value representing the total accumulated wear-generating load and a maximum value assigned to the measuring probe. The remaining operating life or the allowable remaining wear-generating load as well as an overrun beyond the maximum value of the measuring probes that are being monitored can be indicated on a central or decentralized display device of the process system. Of course, for production processes, too, one can assign threshold values and wear-generating load values or corresponding changes in the remaining operating life or the allowable remaining wear-generating load.

In an exemplary embodiment, the measuring probes are equipped with a memory module, for example an EEPROM (Electrically Erasable Programmable Read Only Memory), in which data on the condition of the measuring probe can be stored, specifically the remaining operating life or the allowable remaining wear-generating load and/or the integral value corresponding to the accumulated exposure and/or the maximum exposure value assigned to the measuring probe. It is also possible to store additional parameters, characteristic data and in particular identification data of the measuring probe. The memory module can be arranged for example inside the glass body or in the connector portion of the measuring probe. In other embodiments, the measurement converter can likewise be integrated in the measuring probe. The measurement converter is for example realized by means of an application-specific integrated circuit (ASIC) that includes at least one analog/digital converter, a memory module and a processor.

A memory module that serves to retain data associated with a measuring probe can also be arranged in, or releasably connected or coupled to, any units of the control device or the process control system, such as a measurement converter that is assigned to the measuring probe. The memory module can be a permanently installed memory or a portable memory or data carrier. As a possible example, one can use a portable memory key that is assigned to one or more measuring probes and is connected to an interface, e.g., a USB (Universal Serial Bus) of the process control computer.

Using a memory module that is arranged inside the measuring probe or a portable memory module that is arranged outside the measuring probe can simplify the administration of the measuring probes and improve their portability. The data that are relevant to the administration and operation are stored in the measuring probes themselves, for example by the manufacturer, (e.g., before the probes are put into operation). The stored values can be interrogated by the control device of the system and changed during operation. The essential parts of the administration of the measuring probe are thus taken out of the system control device, which simplifies the operation of the process system. Furthermore, measuring probes can be replaced, whereupon the status data of the newly installed measuring probes are automatically taken over and kept up-to-date. Besides improving the portability of the measuring probes exemplary embodiments can enhance the modular character of the system.

Like the data of the measuring probes, the operating program or programs for executing the method can be either centralized in the process control or decentralized, for example by being arranged, respectively, in the central process control computer or in the measurement converters.

Furthermore, exemplary methods disclosed herein have not only the capability to detect, but also to monitor individual processes, e.g., CIP- and SIP processes. As an example, after a threshold has been exceeded or a corresponding process has been detected, a time interval is set which is associated with the correct execution of the process and within which the monitoring signal should not fall below the threshold value. If the monitoring signal nevertheless falls below the threshold within the time interval, this can be indicated through an appropriate error message.

BRIEF DESCRIPTION OF THE DRAWINGS

Exemplary embodiments will be explained hereinafter in further detail with reference to the drawings, wherein.

DETAILED DESCRIPTION

Figure 1:
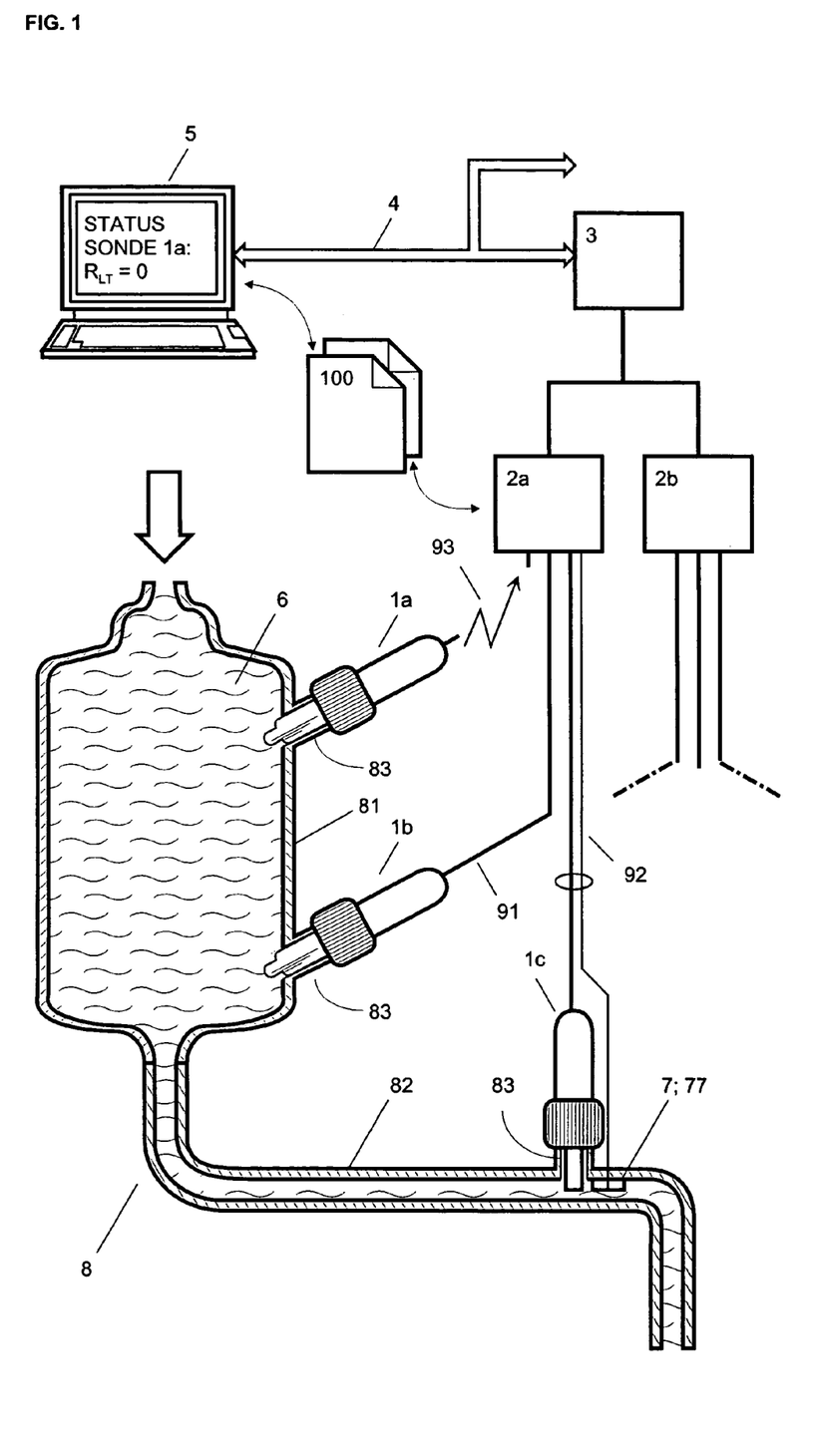
FIG. 1 represents an exemplary single-stage process system with a process vessel 8; 81, 82 in which three measuring probes 1a, 1b, 1c are integrated, which are connected to a process control computer 5 by way of measurement converters 2a, 2b, a segment coupler 3 and a bus system 4.

FIG. 1 represents a process system with one or more stages which operate according to exemplary embodiments of the method, with a process vessel 8 having a container 81 that is filled with the process liquid 6. The container 81 belongs to one process stage and may be connected by means of a connecting pipe 82 to a system unit of a next process stage (see, e.g., the brew stages described in [1]). The properties of the process liquid 6 are measured by means of measuring probes 1a, 1b, 1c, which are connected to a central process control computer 5 by way of cable- and/or wireless connections 91, 92, 93, measurement converters 2a, 2b, a segment coupler 3 and a bus system 4. The measuring probes 1a, 1b, 1c can be installed on the process vessel 8 by means of process couplings and installation armatures 83, as described in [1] and [7], "The InFit® CIP Series: Sanitary Design for the Most Exacting Requirements", company publication of Mettler-Toledo GmbH, CH-8902 Urdorf, Article Number 52 400 526 with a printing date of May 1999. Reference [7] further describes measuring probes, single-rod pH-measuring chains, $O_2$ sensors, conductivity measurement cells and turbidity sensors that can be used with these armatures. Further possibilities also include the use of $CO_2$— and other sensors.

Figure 2:
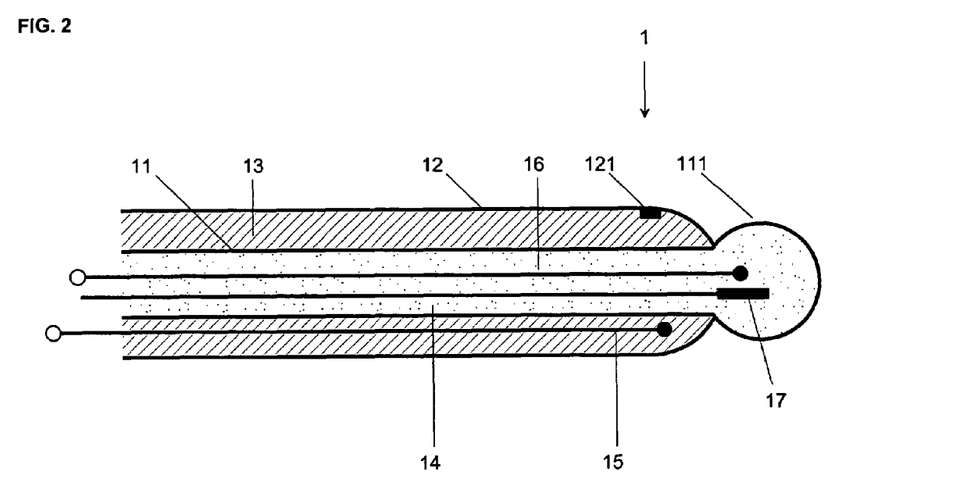
FIG. 2 schematically represents an exemplary measuring probe with a conductor element 16 immersed in an interior buffer 14 in an interior tube 11 and a glass membrane 111, and with a reference element 15 immersed separately in an exterior buffer 13 in an exterior tube 12.

An exemplary principal structure of the pH electrodes, for example in a single-rod configuration with a glass electrode and a reference electrode, is illustrated in FIG. 2. The glass electrode with a conductor element 16 and the reference electrode with a reference element 15 are designed as a combined unit in the form of a measuring probe 1. The conductor element 16 is immersed in a solution of defined pH-value, i.e., an interior buffer 14, inside a first chamber in the interior tube 11 and an adjoining thin-walled glass hemisphere or glass membrane 111. The interior buffer 14 establishes the electrically conductive connection between the inside surface of the glass membrane 111 and the conductor element 16. The voltage potential that exists on the conductor element 16 during the measurement is compared to the voltage potential at a reference element 15 which is immersed inside an exterior tube 12 in an electrolyte or exterior buffer 13 which communicates with the liquid to be measured by slow diffusion through a porous separating wall or diaphragm 121.

Arranged in the interior buffer space is a temperature-measuring sensor 17, by means of which an automatic compensation of temperature effects can be realized. As described in [8], Product Sheet "InPro 2000 pH Electrodes with Liquid Electrolyte and Integrated Temperature Sensor", a company publication of Mettler-Toledo GmbH, CH-8902 Urdorf, with a printing date of October 2000, placing the temperature sensor in a position directly behind the pH-sensitive glass of the glass membrane 111 has the advantage of a fast and highly accurate response of the temperature signal and, accordingly, of the temperature-compensated pH signal.

The temperature-measuring sensor 17 that is integrated in the measuring probe 1 can be used advantageously to carry out an exemplary method which is described hereinafter with reference to FIG. 4. The method can further be performed with a temperature sensor 7 arranged outside of the measuring probe (see FIG. 1), where the temperature sensor 7 measures the temperature of the process liquid or of a cleaning liquid that surrounds or flows past the measuring probe 1 that is being monitored. To perform its function, the temperature sensor 7 can be integrated in a process coupling or an armature 83 that serves for the installation of the measuring probe $1a, \ldots$, and it can be connected to the process control device, such as the measurement converter $2a$, by way of a communication channel 92 with either a wireless or a wire-based arrangement. Methods for a wireless communication between units of a system or a network are described, e.g., in reference [10], U.S. Patent Application Publication 2002/0120750 A1.

Figure 4A:
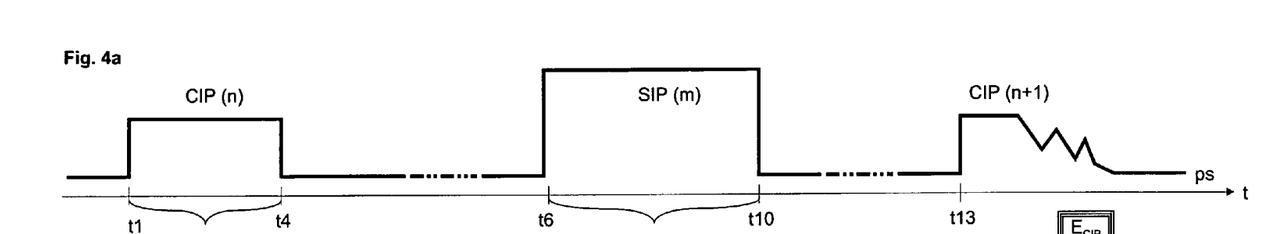
FIG. 4 represents different exemplary time profiles of signals occurring in the process system of FIG. 1.

FIG. 4a illustrates an exemplary time profile of a control signal ps through which CIP- or SIP processes are initiated. At the time t1, a CIP process is started, which ends at the time t4 after a process duration $t_{CIP}$.

Figure 4B:
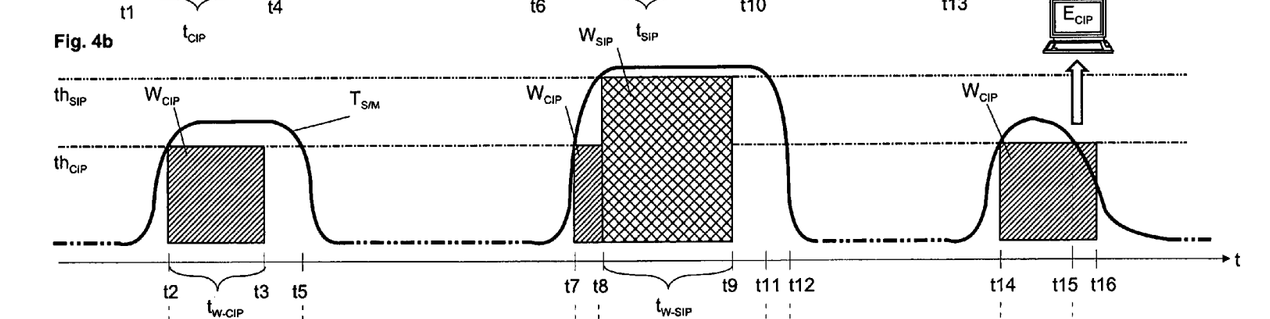

FIG. 4b shows an exemplary time profile of the temperature $T_{S/M}$ of a measuring probe $1a; \ldots$ that is being monitored or of the medium 6 streaming past the measuring probe $1a; \ldots$, for example a cleaning liquid or a process liquid that is being measured by the probe. As the graph shows, after the time t1 the temperature $T_{S/M}$ rises with a slight delay. At the time t2 the temperature moves above a threshold value associated with the CIP process, and after the time t5 the temperature recedes below the threshold again.

According to exemplary embodiments of the invention, the recorded time profile of the temperature $T_{S/M}$ can be evaluated as follows:

On the one hand, based only on the fact that the threshold $th_{CIP}$ associated with the CIP process has been exceeded, the conclusion is drawn that a CIP process has been initiated, which has had an effect on the measuring probe $1a; \ldots$. The remaining operating life $R_{LT}$ or the allowable remaining wear-generating load (hereinafter only referred to as remaining operating life $R_{LT}$ for the sake of simplicity) can therefore be reduced by a certain value. After a certain number of CIP processes have been detected it is therefore possible to determine and to provide notice when the remaining operating life $R_{LT}$ will have been reduced to zero.

The actual downward progress of the remaining operating life $R_{LT}$ can be determined more precisely by also taking the duration of each CIP process into account, which can be determined by registering the time t2 when the temperature rises above the threshold value $th_{CIP}$ and the next following time t5 when the temperature falls below the threshold value $th_{CIP}$ again. Consequently, the remaining operating life $R_{LT}$ is determined based on the integration or summation of the time segments t5-t2 during which the temperature $T_{S/M}$ of the measuring probe 1 lies above the threshold value $th_{CIP}$.

In addition to the cumulative duration of the CIP- or SIP processes, it can be advantageous to also take the accumulated number of CIP- or SIP processes into account, because the wear on the measuring probe at a given cumulative duration value can vary significantly with different accumulated numbers of process cycles. If a large number of temperature rises and -falls, i.e., incidents of traversing the threshold value $th_{CIP}$, has occurred, one normally has to assume a greater wear-generating load on the one or more measuring probes $1a, \ldots$.

As a rule, the temperature levels used in SIP processes are higher than in CIP processes, so that a higher wear-generating load should be assumed. It is possible that only CIP processes or only SIP processes are performed in a process system. However, it is also possible that a number of CIP processes is followed by an SIP process. The choice of whether to perform CIP- or SIP processes depends in each case on the material being processed in the system, the quality requirements, and possibly other process parameters. For example, FIG. 4a illustrates a case where after the CIP process n, an SIP process is initiated at the time t6 and concluded after a time interval $t_{SIP}$ at the time t10. The rise in temperature past the threshold $th_{SIP}$ associated with the SIP process is registered at the time t8, shortly after the time t7 at which the temperature has moved through the threshold $th_{CIP}$ associated with the CIP process. The amount of wear-generating load associated with the individual processes and the reduction in the remaining operating life $R_{LT}$ to be registered for each process can be determined for example by the manufacturer in laboratory tests and stated as the characteristic wear parameter or group of parameters. It is possible to assign respectively different weight factors to the incidents when the temperature rises past the thresholds $th_{CIP}$ or $th_{SIP}$ in order to allow for the disproportionate effects that high temperatures have on the wear-generating load imposed on the one or more measuring probes $1a; \ldots$ and, consequently, on their remaining operating life $R_{LT}$.

It is further possible to determine the wear-generating load on the one or more measuring probes $1a; \ldots$ over the entire operating time. This can be accomplished by integrating the temperature $T_{S/M}$ of the measuring probe 1 over the entire operating time so that not only the wear-generating loads caused by CIP- and/or SIP processes but also the wear effects caused by production processes are accurately taken into account. Thus, the profile of the integral values $INT_{LT}$ also reflects the temperature effects caused by the production processes P(n+1), P(n+2) shown in FIG. 4c. It is therefore possible to introduce additional threshold values that allow production processes or at least wear-generating loads on the measuring probe 1 to be detected and accounted for. Thus, during the production processes, the material in process constitutes the medium 6 which causes on the one hand the wear-generating load on the measuring probe $1a, \ldots$ and on the other hand provides the information regarding the wear-generating load to the temperature sensor 7; 17, while during the cleaning processes the medium 6 is constituted by the cleaning medium (steam or liquid).

Figure 4C:
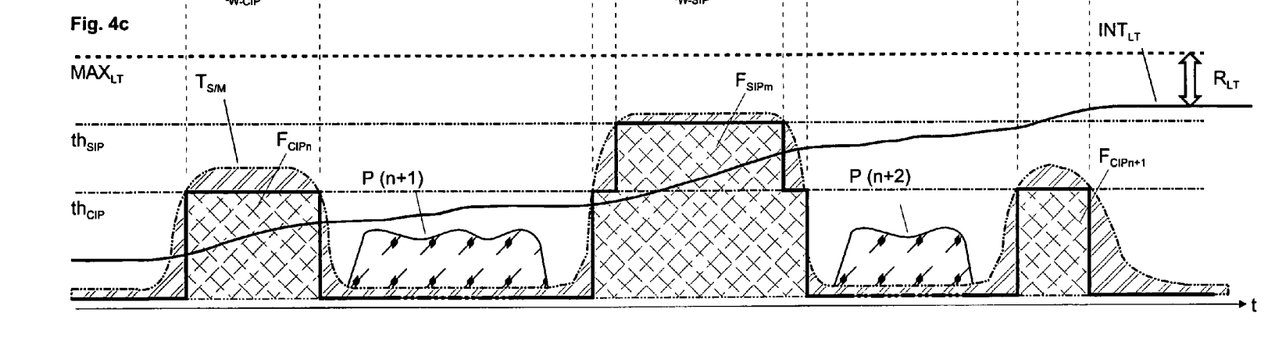

As may be seen in FIG. 4c, the curve representing the integral values $INT_{LT}$ as a function of time increases continuously towards a maximum value $MAX_{LT}$. The difference between the maximum value $MAX_{LT}$ and the integral value $INT_{LT}$ existing at a given time determines the remaining operating life $R_{LT}$ ($R_{LT}=MAX_{LT}-INT_{LT}$) of the measuring probe 1a, . . . .

Either the calculated remaining operating life $R_{LT}$ or only the fact that it has crossed the zero level can be indicated for each of the monitored measuring probes 1a; . . . on a central or decentralized display device 2a, 5 of the process system.

Figure 3:
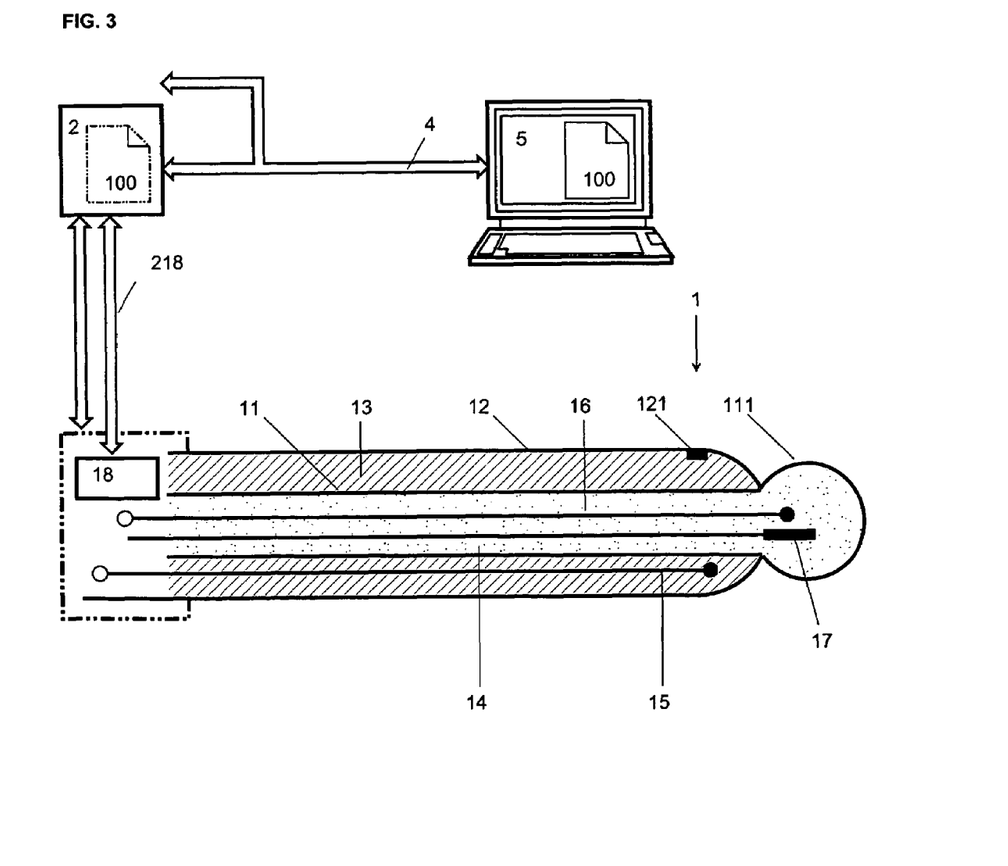
FIG. 3 represents the exemplary measuring probe 1 of FIG. 2 with a memory module 18 in which the data of the measuring probe 1 can be stored.

As shown in FIG. 3, the measuring probes 1 an exemplary embodiment include a memory module 18 which is integrated, e.g., into the glass body or the connector plug portion of the measuring probe 1. The memory module 18 serves to store the condition of the measuring probe 1, specifically the maximum value $MAX_{LT}$ assigned to the measuring probe 1, the registered integral value $INT_{LT}$, the characteristic wear parameter and/or the remaining operating life $R_{LT}$. This can simplify the administration of the measuring probes of a process system. Any or all of the data required for the operation and the monitoring of the measuring probe 1 can be stored in the memory module 18, so that the measuring probe 1 can be connected to a measurement converter or transmitter 2a; 2b; . . . and put into operation without further administrative procedures. The measuring probe 1 which is equipped with the memory module 18 can thus be moved without any problems from a first to a second place of installation even after it has been put into operation. The memory module 18 can include, e.g., an EEPROM module (Electrically Erasable Programmable Read Only Memory) as described in reference [9], U. Tietze, Ch. Schenk, "Halbleiterschaltungstechnik" (Semiconductor Circuit Design), 11$^{th}$ edition, 2$^{nd}$ printing, published by Springer Verlag, Berlin 1999, pages 751-752. In further exemplary embodiments, the associated measurement converter 2 can likewise be integrated in the measuring probe 1.

Exemplary methods disclosed herein further offer the possibility of monitoring the processes, e.g., CIP- or SIP processes, after they have been detected. For example, after the temperature has risen above a threshold value $th_{CIP}$ or $th_{SIP}$, in other words after a CIP- or SIP process has been detected, a time interval $t_{W-CIP}$ or $t_{W-SIP}$ is set which is associated with the correct execution of the process and within which the monitoring signal should not fall below the respective threshold value $th_{CIP}$ or $th_{SIP}$. If the monitoring signal nevertheless falls below the threshold $th_{CIP}$ or $th_{SIP}$ within the respective time interval $t_{W-CIP}$ or $t_{W-SIP}$, this can be indicated through an appropriate error message. The corresponding surveillance windows $W_{CIP}$ and $W_{SIP}$ which are opened after the respective threshold value $th_{CIP}$ or $th_{SIP}$ has been exceeded are marked in FIG. 4b. As shown in FIG. 4b, when at the beginning of an SIP process the lower threshold $th_{CIP}$ is passed, a surveillance window $W_{CIP}$ is opened at first but is overwritten by the surveillance window $W_{SIP}$ when the temperature rises above the upper threshold value $th_{SIP}$.

FIGS. 4a and 4b illustrate a case where a malfunction occurs in the CIP process n+1, so that the graph cuts through the surveillance window $W_{CIP}$ and an error $E_{CIP}$ is signaled. If during an SIP process the temperature graph cuts through the corresponding surveillance window $W_{SIP}$, this will likewise trigger an error signal.

Exemplary methods have been described and illustrated. However, based on the teachings discussed, a person skilled in the relevant art will be able to realize further embodiments. In particular, it is possible to use further parameters for the identification of the individual CIP- and SIP processes. For example by measuring the pressure in the process vessel, it is possible to distinguish CIP processes in which liquids are used from those in which steam is used. It can therefore be advantageous to add a pressure sensor 77 (see FIG. 1) to the process system or to the measuring probes. Methods and sensors for measuring pressure are described in reference [9], pages 1241 to 1251. The measuring probe 1 that is equipped with the memory module 18 can further be used for storing additional data.

Exemplary methods discussed herein can be carried out by means of centralized or decentralized parts of the control device, with the process control computer 5 and/or the measurement converters or transmitters 2a, . . . , which are equipped for this purpose with the appropriate operating programs 100 (see FIG. 1). The condition of the measuring probes 1 can be indicated, e.g., on the process computer 5 alone, or on the measuring converters or transmitters 2a, . . . . It is also possible to split the tasks between the different levels of the process control. With measures that are known to those of ordinary skill in the art, the inventive method can thus be implemented at low cost in single-stage or multi-stage process systems of any kind.

All of the foregoing documents mentioned herein are incorporated by reference in their entireties.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. Method for determining the condition of at least one measuring probe which is integrated in a process vessel to measure a process parameter and which is cleaned from time to time using at least one of CIP- and SIP processes without uninstalling the measuring probe from the process vessel, comprising:
   measuring a temperature ($T_{S/M}$) of the measuring probe or of a medium surrounding the measuring probe with a measuring sensor arranged inside the measuring probe or inside the process vessel; and
   determining a condition of the measuring probe based on a record of the temperature ($T_{S/M}$) measured over time after the installation of the measuring probe.

2. Method according to claim 1, comprising:
   comparing the temperature ($T_{S/M}$) to at least one threshold value ($th_{CIP}$; $th_{SIP}$), and when said at least one threshold value has been exceeded:
   a) a wear-generating load is registered according to the threshold value ($th_{CIP}$; $th_{SIP}$) that has been exceeded;
   b) a wear-generating load is registered according to the threshold value ($th_{CIP}$; $th_{SIP}$) that has been exceeded, and a cumulative sum ($INT_{LT}$) of all wear-generating loads is calculated; or
   c) a wear-generating load is registered according to the threshold value ($th_{CIP}$; $th_{SIP}$) that has been exceeded, the cumulative sum ($INT_{LT}$) of all wear-generating loads is calculated, and by comparing the sum ($INT_{LT}$) to a maximum value ($MAX_{LT}$) for an allowable cumulative load, a remaining allowable load or remaining operating lifetime ($R_{LT}$) is determined.

3. Method according to claim 2, wherein when said at least one threshold value ($th_{CIP}$; $th_{SIP}$) has been exceeded, a process control device monitors execution of a process (CIP; SIP) associated with a respective one of said at least one threshold value ($th_{CIP}$; $th_{SIP}$).

4. Method according to claim 3, wherein when said at least one threshold value ($th_{CIP}$; $th_{SIP}$) has been exceeded, a time interval ($t_{CIP}$, $t_{SIP}$) is set which corresponds to a correct execution of a respective process (CIP; SIP), where within said time interval ($t_{CIP}$, $t_{SIP}$) the temperature ($T_{S/M}$) should not fall below the threshold value ($th_{CIP}$; $th_{SIP}$), but if said temperature ($T_{S/M}$) nevertheless falls below the threshold value within said time interval ($t_{CIP}$, $t_{SIP}$), an error message ($E_{CIP}$; $E_{SIP}$) is generated.

5. Method according to claim 2, comprising:
reducing a remaining allowable load or remaining operating lifetime ($R_{LT}$) of the measuring probe by an amount corresponding to the threshold ($th_{CIP}$, $th_{SIP}$) which is assigned to a process performed.

6. Method according to claim 5, wherein the process performed is a cleaning process CIP or a sterilizing process SIP.

7. Method according to claim 2, wherein the sum ($INT_{LT}$) of all wear-generating loads to which the measuring probe is exposed is determined by integrating
  a) a recorded temperature ($T_{S/M}$) over an entire time span, or
  b) a recorded temperature ($T_{S/M}$) from a time when a threshold value ($T_{CIP}$; $th_{SIP}$) was exceeded, or
  c) a recorded temperature ($T_{S/M}$) over time segments (t5-t2), (t12-t7), (t15-t14) during which the temperature ($T_{S/M}$) exceeds respective threshold values ($th_{CIP}$, $th_{SIP}$),
and wherein when a maximum value ($MAX_{LT}$) has been exceeded, a condition of the measuring probe or an indication that the maximum value ($MAX_{LT}$) has been exceeded is reported.

8. Method according to claim 1, wherein data concerning administration and/or operation of the measuring probe, are stored in a memory module contained inside the measuring probe or on a fixed or portable data carrier arranged outside the measuring probe.

9. Method according to claim 8, wherein the data concern at least one of an allowable remaining load or the remaining operating lifetime ($R_{LT}$), a cumulative load ($INT_{LT}$), a characteristic wear parameter, a maximum value ($MAX_{LT}$) and/or identification data.

10. Measuring probe for executing the method according to claim 1, wherein the measuring probe includes a memory module in which the data required for the operation and monitoring the measuring probe are stored.

11. Measuring probe according to claim 10, wherein the measuring probe is configured to measure conductivity, pH value, turbidity, oxygen content or $CO_2$ content of a medium.

12. Measuring probe according to claim 11, wherein the data includes a remaining operating lifetime ($R_{LT}$), an integral value ($INT_{LT}$), a characteristic wear parameter, a maximum value ($MAX_{LT}$), and/or identification data.

13. Process system for executing the method according to claim 1, comprising:
  a process vessel;
  at least one measuring probe integrated in the process vessel;
  at least one measurement—and/or control device operable to measure the temperature ($T_{S/M}$) of the measuring probe or of the medium surrounding the measuring probe, and operable to register a record of the temperature ($T_{S/M}$) measured over time during use of the measuring probe and to determine a condition of the measuring probe; and
  at least one operating program in a process control computer and/or in a measurement converter, said process control computer and/or measurement converter being connected by way of a wireless or wire-based arrangement to the measuring probe and/or to the temperature measuring sensor or a pressure sensor.

14. Process system according to claim 13, wherein the temperature ($T_{S/M}$) can be measured by means of a measurement sensor which is arranged inside the measuring probe or inside the process vessel or, if applicable, inside an armature serving as an installation mount for the measuring probe.

15. Process system according to claim 13, wherein the at least one measuring probe is provided in which a memory module and/or a measurement converter is integrated.

16. Process system according to claim 13, wherein the method executed includes cleaning and/or sterilizing the process vessel using at least one of CIP and SIP processes without uninstalling the measuring probe.

* * * * *